(12) United States Patent
Xie et al.

(10) Patent No.: US 12,396,990 B2
(45) Date of Patent: Aug. 26, 2025

(54) APPLICATION OF 5-HYDROXYTRYPTAMINE RECEPTOR 1A IN PREPARING DRUG FOR PORTAL HYPERTENSION

(71) Applicant: SECOND AFFILIATED HOSPITAL, SECOND MILITARY MEDICAL UNIVERSITY, Shanghai (CN)

(72) Inventors: Wei-Fen Xie, Shanghai (CN); Chang-Peng Zhu, Shanghai (CN); Xin Zhang, Shanghai (CN)

(73) Assignee: SECOND AFFILIATED HOSPITAL, SECOND MILITARY MEDICAL UNIVERSITY, Shanghai (CN)

( * ) Notice: Subject to any disclaimer, the term of this patent is extended or adjusted under 35 U.S.C. 154(b) by 552 days.

(21) Appl. No.: 16/965,903

(22) PCT Filed: Jan. 17, 2019

(86) PCT No.: PCT/CN2019/072124
§ 371 (c)(1),
(2) Date: Jul. 29, 2020

(87) PCT Pub. No.: WO2019/149079
PCT Pub. Date: Aug. 8, 2019

(65) Prior Publication Data
US 2021/0038595 A1    Feb. 11, 2021

(30) Foreign Application Priority Data
Jan. 30, 2018  (CN) .......................... 201810090563.2

(51) Int. Cl.
| | | |
|---|---|---|
| *A61P 9/12* | (2006.01) | |
| *A61K 31/137* | (2006.01) | |
| *A61K 31/496* | (2006.01) | |
| *A61K 45/06* | (2006.01) | |

(52) U.S. Cl.
CPC .......... *A61K 31/496* (2013.01); *A61K 31/137* (2013.01); *A61P 9/12* (2018.01); *A61K 45/06* (2013.01)

(58) Field of Classification Search
CPC ........ A61K 31/496; A61K 31/137; A61P 9/12
See application file for complete search history.

(56) References Cited

U.S. PATENT DOCUMENTS

2016/0375016 A1   12/2016  Kaplin et al.

FOREIGN PATENT DOCUMENTS

| | | |
|---|---|---|
| CN | 101766588 A | 7/2010 |
| WO | 9710824 A1 | 3/1997 |
| WO | 9929323 A1 | 6/1999 |
| WO | 2011009012 A1 | 1/2011 |

OTHER PUBLICATIONS

Zaretsky et al., Neuroscience Letters, 2015, pp. 215-219.*
Coelho et al., Journal of Pharmacy and Pharmacology, 2001, 53: 1419-1426.*
International Search Report of PCT/CN2019/072124.
Written Opinion of PCT/CN2019/072124.
Coelho, A.-M. et al. "Rectal antinociceptive properties of alverine citrate are linked to antagonism at the 5-HT1A receptor subtype" Journal of Pharmacy and Pharmacology, vol. 53, Dec. 31, 2001 (Dec. 31, 2001), ISSN: 0022-3573.
Rahn, K. A. et al. "The role of 5-HT1A receptors in mediating acute negative effects of antidepressants: implications in pediatric depression" Translational Psychiatry, vol. 5, May 5, 2015 (May 5, 2015), Entire document.
Ruddell, R. G. et al. "The function of serotonin within the liver" Journal ofHepatology, vol. 48, Dec. 31, 2008 (Dec. 31, 2008), ISSN: 0168-8278, Entire document.
(Shi, Xianyan et al.). (Nonofficial translation: Changes of Five Plasma Biogenic Amines in Patients with Liver Cirrhosis and Their Clinical Significance) (Journal of Clinical Hepatology ), vol. 9, No. 4, Dec. 31, 1993 (Dec. 31, 1993), Entire document.
(Zhang, Xiaobing). (Non-official translation: Section 2 Portal Hypertension) (Non-official translation: Diagnosis and Treatment of Common Clinical Diseases), Mar. 31, 2016 (Mar. 31, 2016), Entire document.
(Ma, Yunhan et al.).(Non-official translation: Serotonin Promoting the Development and Progression of Hepatocellular Carcinoma) Tumor), vol. 36, No. 5, May 31, 2016 (May 31, 2016), Entire document.

* cited by examiner

*Primary Examiner* — Shobha Kantamneni (57) ABSTRACT

The present invention relates to the technical field of pharmaceuticals and specifically describes an application of a 5-hydroxytryptamine receptor 1A in preparing a drug for portal hypertension. The present invention achieved a significant decrease in portal venous pressure in model rats with cirrhotic portal hypertension by means of an HTR1A inhibitor WAY100635 administered at 1 mg/kg/day by intraperitoneal injection or alverine administered at 15 mg/kg/day by oral gavage. A 5-hydroxytryptamine receptor 1A antagonist can be used to prepare an experimental drug for the treatment of cirrhotic portal hypertension. Furthermore, the 5-hydroxytryptamine receptor 1A antagonist can also be used to prepare drugs for symptoms of portal hypertension syndrome, such as esophageal and fundal varices, rupture and bleeding, ascites, or hepatic encephalopathy. The present invention provides a novel treatment means to treat the manifestations of portal hypertension syndrome, such as esophageal and fundal varices, rupture and bleeding, ascites, or hepatic encephalopathy.

5 Claims, 6 Drawing Sheets

APPLICATION OF 5-HYDROXYTRYPTAMINE RECEPTOR 1A IN PREPARING DRUG FOR PORTAL HYPERTENSION

CROSS-REFERENCE TO RELATED APPLICATIONS

This application is a national stage application of PCT Application No. PCT/CN2019/072124. This Application claims priority from PCT Application No. PCT/CN2019/072124, filed Jan. 17, 2019, CN Application No. CN 201810090563.2, filed Jan. 30, 2017, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference were individually incorporated by reference.

FIELD OF THE INVENTION

The present invention relates to the technical field of pharmaceuticals and specifically describes an application of the 5-hydroxytryptamine receptor 1A in preparing a drug for treating portal hypertension and its complications, such as esophagogastric varices, variceal hemorrhage, ascites, or hepatic encephalopathy.

BACKGROUND OF THE INVENTION

The 5-hydroxytryptamine receptor 1A (also known as serotonin 1A receptor, 5-HT1A receptor, HTR1A) is one of the various subtypes of 5-hydroxytryptamine (5-HT) receptors, which belongs to G-protein coupled receptors (GPCRs) family and has diverse physiological actions through coupling with Gi/o protein. HTR1A is widely distributed in organs and tissues of the whole body, mainly the central nervous system, and expresses in the regions such as the middle ganglion nucleus of the brain stem, hippocampus, lateral septum, amygdala, etc., and plays an important role in the progress of neuromodulation, blood pressure regulation, and thermoregulation. Currently, targeting HTR1A is mainly used for the treatment of disorders caused by serotonergic neuronal dysfunction, such as anxiety, depression, limb movement disorders, pain, schizophrenia, and so on.

Chronic liver disease (CLD) is one of the major global burden diseases. CLDs induced by hepatitis viruses infection, drug injury, immunologic injury, alcohol abuse, metabolic disorders, can progress to liver cirrhosis and lead to portal hypertension (PH). PH is characterized by a pathologic increase of portal pressure due to increased outflow resistance and/or increased portal blood flow. PH can further cause a series of complications, such as ascites, hypersplenism, esophagogastric varices, hepatic encephalopathy, and so on. All these complications affect the prognosis of patients with cirrhosis, and variceal hemorrhage is the leading cause of death caused by liver cirrhosis. Therefore, the treatment of PH is crucial for preventing and treatment of esophagogastric varices and variceal hemorrhage, ascites, hepatic encephalopathy, and so on.

Current treatments for PH in clinical practice include pharmacologic therapies and non-pharmacologic therapies. Pharmacologic therapies contain the use of splanchnic vasoconstrictors (such as vasopressin, terlipressin, somatostatin and its analogues, nonselective β-blockers such as propranolol, carvedilol) and intrahepatic vasorelaxants (such as nitrates, simvastatin, adrenergic receptor blockers prazosin, clonidine, angiotensin blockers captopril, losartan, irbesartan, and so on). Non-pharmacologic therapies consist of endoscopic variceal ligation (EVL), transjugular intrahepatic portosystemic shunt (TIPS), and others. Such approaches, however, do not adequately cure or ameliorate PH, mainly due to the unsatisfactory therapeutic effect or adverse effects. Accordingly, it is urgent to develop a novel treatment for PH to improve therapeutic effect without obvious side effect.

Therefore, a heretofore unaddressed need exists in the art to address the aforementioned deficiencies and inadequacies.

SUMMARY OF THE INVENTION

The present invention aims to provide an application of 5-hydroxytryptamine receptor 1A as a target in preparing drugs for portal hypertension and its complications such as esophagogastric varices, variceal hemorrhage, ascites, or hepatic encephalopathy.

Another objective of the present invention is to provide a method for treating portal hypertension and its complications such as esophagogastric varices, variceal hemorrhage, ascites, or hepatic encephalopathy.

In order to achieve the purposes, the technical scheme adopted by the present invention is described as follows:

In one aspect, the present invention provides a target for treating portal hypertension, that is 5-hydroxytryptamine receptor 1A (5-HT1A receptor, serotonin 1A receptor, HTR1A).

The present invention used two rat models of cirrhotic portal hypertension induced by thioacetamide (TAA) and carbon tetrachloride ($CCl_4$), and results showed that intraperitoneally injection of WAY 100635 (selective antagonist of HTR1A) at a dose of 1 mg/kg or delivery of alverine by gavage at a dose of 15 mg/kg once per day can significantly decrease portal pressure of rats in the two models of cirrhotic portal hypertension.

The present invention used the rat model of cirrhotic portal hypertension induced by carbon tetrachloride ($CCl_4$), and found that intraperitoneally injection of 8-OH-DPAT (selective agonist of HTR1A) at a dose of 1 mg/kg once per day can significantly increase portal pressure of rats of cirrhotic portal hypertension.

In an alternative aspect, the present invention provides an application of the 5-hydroxytryptamine receptor 1A in preparing drugs for treating portal hypertension.

Further, the portal hypertension mentioned herein is esophagogastric varices, variceal hemorrhage, ascites, hepatic encephalopathy, experimental cirrhosis, and so on.

Further, the drug for the treatment portal hypertension mentioned herein uses 5-hydroxytryptamine receptor 1A as an intervention target for the treatment of portal hypertension.

Further, the active ingredient of the drug for the treatment portal hypertension mentioned herein is a reagent that inhibits the activity or expression of 5-hydroxytryptamine receptor 1A.

In an alternative aspect, the present invention provides an application of reagents that inhibit the activity or expression of 5-hydroxytryptamine receptor 1A in preparing drugs for treating portal hypertension.

Further, the reagents that inhibit the activity or expression of 5-hydroxytryptamine receptor 1A mentioned herein include but are not limited to selective or non-selective antagonists of 5-hydroxytryptamine receptor 1A, full or part antagonists of 5-hydroxytryptamine receptor 1A, and so on.

Further, the reagents that inhibit the activity or expression of 5-hydroxytryptamine receptor 1A mentioned herein can be given orally, intraperitoneally, intravenously, and so on.

In the preferred embodiment of the present invention, the reagents that inhibit the activity or expression of 5-hydroxytryptamine receptor 1A mentioned herein are WAY 100635 or alverine.

More preferably, the reagents that inhibit the activity or expression of HTR1A are specifically: intraperitoneal injection of WAY 100635 at a dose of 1 mg/kg; administration of alverine by gavage at a dose of 15 mg/kg.

In another aspect, the present invention provides a drug for the treatment of portal hypertension, wherein the drug for the treatment of portal hypertension contains a reagent for inhibiting the activity or expression of 5-hydroxytryptamine receptor 1A.

Further, the drugs for the treatment of portal hypertension mentioned herein include other pharmacologically acceptable ingredients.

Preferably, the other pharmacologically acceptable ingredient mentioned herein is a drug that has no antagonistic effect with 5-hydroxytryptamine receptor 1A antagonist, or one or more pharmaceutical excipients permitted.

The drugs for the treatment of portal hypertension mentioned herein can be made into a pharmaceutical preparation together with a conventional pharmaceutical auxiliary material in pharmacy.

The dosage forms of the pharmaceutical preparation are injection, capsule, tablet, powder, granules, pill, microcapsule and microsphere preparation, suppository, ointment, powder injection, aerosol, spray, or targeted preparation.

The advantages and beneficial effects of the present invention are as follows:

The present invention provides an application of using 5-hydroxytryptamine receptor 1A (HTR1A) as a target in preparing a drug for treating portal hypertension, and specifically provides an application of targeting HTR1A in preparing drugs for treating portal hypertension and its complications such as esophagogastric varices, variceal hemorrhage, ascites, hepatic encephalopathy, and experimental cirrhotic portal hypertension. The present invention used two rat models of cirrhotic portal hypertension induced by thioacetamide (TAA) and carbon tetrachloride ($CCl_4$), and the data showed that intraperitoneally injection of WAY 100635 (selective antagonist of HTR1A) at a dose of 1 mg/kg or delivery of alverine by gavage at a dose of 15 mg/kg once per day can significantly decrease portal pressure of rats in the two models of cirrhotic portal hypertension. Accordingly, a 5-hydroxytryptamine receptor 1A antagonist can be used to prepare a drug for the treatment experimental portal hypertension. Furthermore, the 5-hydroxytryptamine receptor 1A antagonist can also be used to prepare drugs for complications of portal hypertension, such as esophagogastric varices, variceal hemorrhage, ascites, or hepatic encephalopathy. The present invention provides a novel method for clinical treatment of portal hypertension and its complications, such as esophagogastric varices, ascites, or hepatic encephalopathy.

DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

Having described the invention in general terms, reference will now be made to the accompanying drawings.

EMBODIMENT EXAMPLES

The following is detailed description of the specific embodiment provided by the invention in combination with the embodiments. The persons skilled in the relevant field should understand that what is described in detail below is illustrative but not restrictive, which shall not limit the scope of protection of the invention.

The no specifically indicated experimental methods herein described are under conventional conditions, all the reagents used are purchased routinely from the market.

Example 1

Effects of the selective antagonist of HTR1A WAY 100635, and alverine on portal pressure (PP) in cirrhotic portal hypertensive rats induced by thioacetamide (TAA).

1. Experimental Animals

Male Wistar rats, weighting about 140 to 160 grams (g) each, were purchased from SLAC Laboratory Animal Co., Ltd (Shanghai, China) and housed under standard animal laboratory conditions in the experimental animal center of Second Military Medical University (Shanghai, China). All animal experiments in this study were performed in accordance with protocols approved by the local Ethical Committee of the Second Military Medical University.

2. Animal Model and Treatment

1) Thirty-five male Wistar rats, weighting 140 g to 160 g, were randomly divided into normal control group (N=8) and TAA group (N=27). Rats in TAA group were subjected to intraperitoneally (i.p.) injections of TAA (purchase from ???) at 200 mg/kg, which is diluted in sterile normal saline (NS; 0.9% sodium chloride), 3 times per week for 16 weeks to induce cirrhotic portal hypertension. The normal controls received injections of NS at the same timepoint. At the beginning of the $17^{th}$ week, rats in TAA group were randomly divided into four groups: Vehicle group (N=7), Alverine group (N=7), WAY 100635 group (N=7), and carvedilol group (N=6).

2) Alverine (purchase from TargetMol) was diluted in the saline at a concentration of 5 mg/ml and delivered to the rats in Alverine group via gavage (p.o.). WAY 100635 (purchase from Selleck) was diluted in sterile normal saline at a concentration of 1 mg/ml and peritoneally injected (i.p.) into the rats in WAY 100635 group. Carvedilol (purchase from TargetMol) was diluted in sterile normal saline at a concentration of 1 mg/ml and delivered to the rats in carvedilol group via gavage.

3) Rats in the Alverine group, WAY 100635 group, and carvedilol group were received alverine 15 mg/kg p.o.+ saline i.p., saline p.o.+WAY 100635 1 mg/kg i.p., carvedilol 10 mg/kg p.o.+saline i.p., respectively once per day for one week, while rats in vehicle group received saline p.o. and saline i.p. at the same timepoint.

4) After one-week treatment, portal pressure of all the rats were measured and rats were sacrificed for liver tissues.

3. Measurement of Portal Pressure in Rats

1) Self-made portal pressure measuring kit, which contains 24-Gauge scalp vein set (Y type) and catheter, and high-sensitive pressure sensor, biological signal processing system (SMUP-U, Jide experimental teaching equipment factory, Shanghai, China) were used to measure the portal pressure in rats.

2) Connect all the catheters and device, check the tightness and set zero, then open the portal pressure measuring kit, connect the catheter with the scalp vein set and high-sensitive pressure sensor, following the connection between pressure sensor and biological signal processing system. Fill all the catheters with heparin sodium saline (volume of heparin sodium and saline: 1.25 WU: 500 ml), eliminate the air bubbles and close the catheter. Then remove the needle in the scalp vein set, place it horizontally at the portal vein height of the rat (supine position). The zero point was set after opening the catheter in the biological collection system software.

3) Rats were anesthetized with inhalational isopentane through a mask. A midline abdominal incision was made, and the portal vein was cannulated with a 24-Gauge scalp vein set, connecting with a catheter filled heparin-saline, to measure PP.

4. Histologically Examination of Rat Livers

After measurement of portal pressure, the rat livers were isolated and fixed with 10% neutral formaldehyde, and then dehydrated and embedded in paraffin. Liver sections (3 μm) were made and baked at 65° C. for 2 hours. Hematoxylin-eosin (HE) staining or Sirius red staining were then performed and observed under microscope. Images of HE staining and Sirius red staining were taken.

5. Statistically Analysis

Data were presented as the means ±SEM. One-way analysis of variance (ANOVA) and student's t-tests were performed to compare data between two groups, and a P value of less than 0.05 was considered statistically significant.

6. Results

Figure 1:
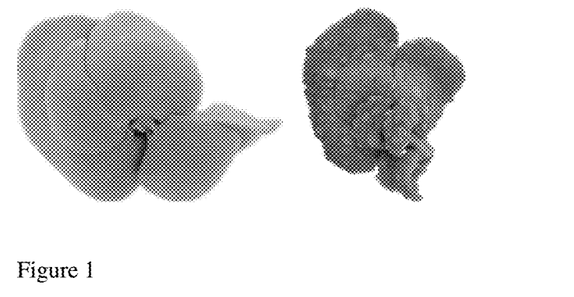
FIG. 1 presents representative images of livers from thioacetamide (TAA) induced cirrhotic rats (left) and normal controls (right).

1) Gross Morphology of Livers from TAA Induced Cirrhotic Rats and Normal Controls Liver specimens were obtained after TAA induction, treatment, and measurement of portal pressure. As shown in FIG. 1 from general observation, livers from TAA group had a significant small size and nodular hyperplasia on the surface of liver, while livers from normal controls had smooth surface without nodular hyperplasia.

2) HE Staining of Livers from TAA Induced Cirrhotic Rats and Normal Controls

Figure 2:
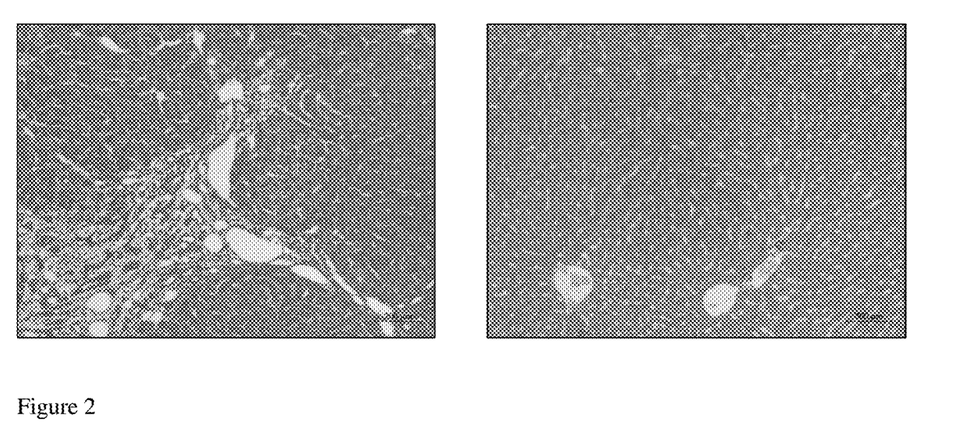
FIG. 2 presents representative images of HE staining of liver sections in TAA induced cirrhotic rats (left) and normal controls (right).

As shown in FIG. 2, HE staining showed normal histology of liver with normal lobules, portal area, and interlobular septum in the liver from normal rats. In the TAA induced cirrhotic rats, parenchymal fibrous tissue and pseudo-lobules were found in livers.

Figure 3:
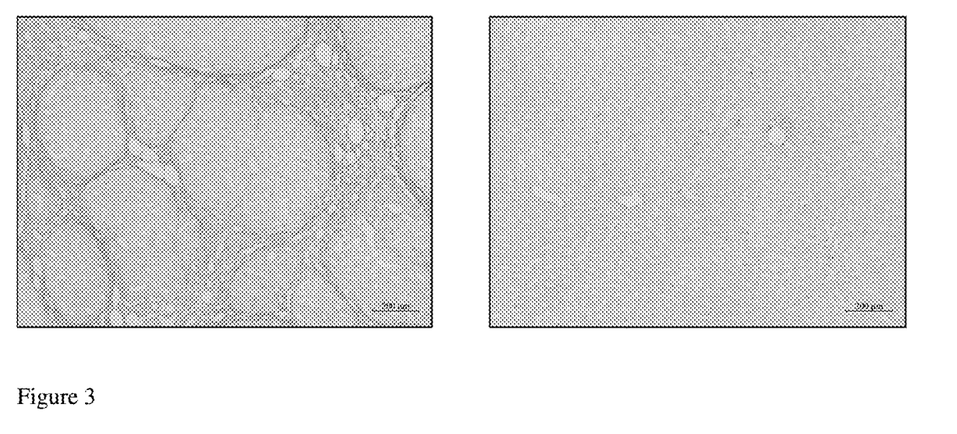
FIG. 3 presents representative images of Sirius Red staining of liver sections in TAA induced cirrhotic rats (left) and normal controls (right).

3) Sirius Red Staining of Livers from TAA Induced Cirrhotic Rats and Normal Controls As shown in FIG. 3, Sirius red staining showed there were a large amount of collagen deposition in the livers from TAA induced cirrhotic rats, while only a little collagen deposition was found in the normal interlobular septum and portal area in the livers from normal controls.

Figure 4:
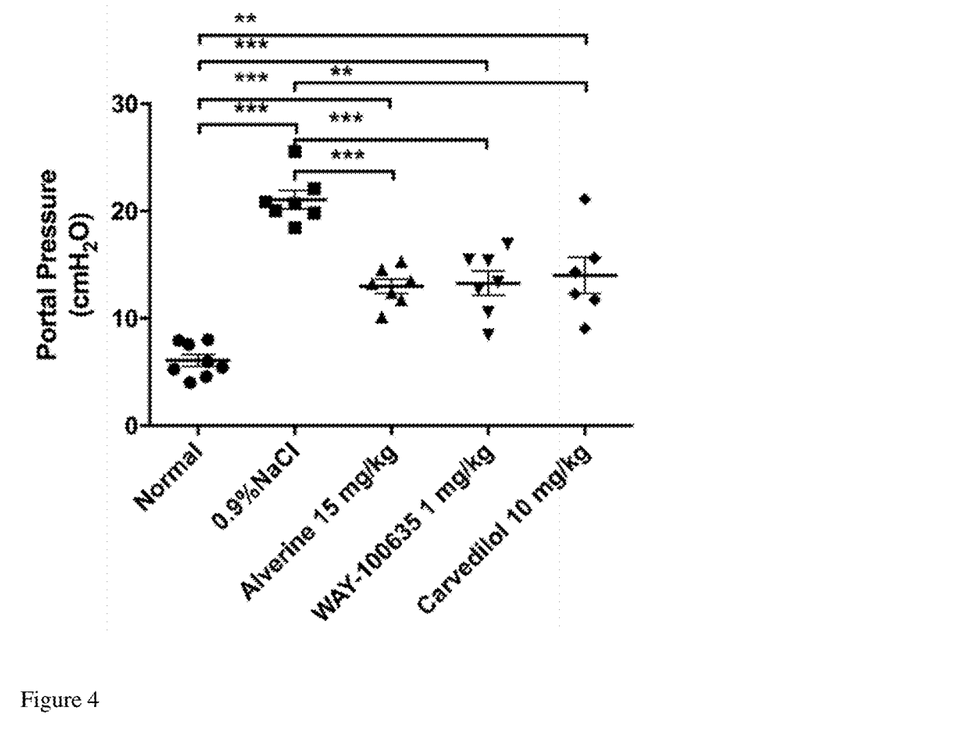
FIG. 4 shows effects of alverine and WAY 100635 on portal pressure (PP) in cirrhotic portal hypertensive rats induced by TAA. PP: Vehicle vs. Normal control, P<0.0001; Alverine vs. Normal control, P<0.0001; WAY 100635 vs. Normal control, P<0.0001; Carvedilol vs. Normal control, P=0.0043; Alverine vs. Vehicle, P<0.0001; WAY 100635 vs. Vehicle, P=0.0001; Carvedilol vs. Vehicle, P=0.0025.

4) Portal pressure of rats in different groups were showed in FIG. 4 and Table 1. Portal pressure: Vehicle vs. Normal control, P<0.0001; Alverine vs. Normal control, P<0.0001; WAY 100635 vs. Normal control, P<0.0001; Carvedilol vs. Normal control, P=0.0043; Alverine vs. Vehicle, P<0.0001; WAY 100635 vs. Vehicle, P=0.0001; Carvedilol vs. Vehicle, P=0.0025.

TABLE 1

Portal pressure of rats in TAA model.

| Groups | Portal pressure (cmH$_2$O) |
|---|---|
| Normal control | 6.10 ± 1.56 |
| Vehicle | 21.07 ± 2.27 |
| Alverine | 12.98 ± 1.74 |
|  | (−38.39%[#], P < 0.0001) |
| WAY10063 | 13.27 ± 3.00 |
|  | (−37.04%[#], P = 0.0001) |
| Carvedilol | 14.01 ± 4.14 |
|  | (−33.54%[#], P = 0.0025) |

[#]vs. Vehicle, Student't test.

As shown in Table 1, the selective antagonist of HTR1A WAY 100635 and alverine significantly decreased portal pressure of TAA induced portal hypertensive rats comparing to that of normal controls. Additionally, the effect of WAY 100635 and alverine were not significantly different from that of carvedilol.

Example 2

Effects of the selective antagonist of HTR1A WAY 100635, and alverine on portal pressure (PP) in cirrhotic portal hypertensive rats induced by carbon tetrachloride (CCl$_4$).

1. Experimental Animals

Similar as that in embodiment example 1.

2. Animal Model and Treatment

1) Thirty-one male Wistar rats, weighting 140 g to 160 g, were randomly divided into normal control group (N=7) and CCl$_4$ group (N=24). Rats in CCl$_4$ group were subjected to intraperitoneally (i.p.) injections of CCl$_4$ at 0.25 ml/kg (diluted 1:3 v/v in olive oil) twice per week for 12 weeks to induce cirrhotic portal hypertension, while the normal controls received injections of olive oil at the same timepoint. At the beginning of the eleventh week, rats in CCl$_4$ group were randomly divided into four groups: Vehicle group (N=7), Alverine group (N=6), WAY 100635 group (N=5), and carvedilol group (N=6).

2) Alverine was diluted in sterile normal saline at a concentration of 5 mg/ml and delivered to the rats in Alverine group via gavage (p.o.). WAY 100635 was diluted in sterile normal saline at a concentration of 1 mg/ml and peritoneally injected (i.p.) into the rats in WAY 100635 group. Carvedilol was diluted in sterile normal saline at a concentration of 1 mg/ml and delivered to the rats in carvedilol group via gavage.

3) Rats in the Alverine group, WAY 100635 group, and carvedilol group were received alverine 15 mg/kg p.o.+saline i.p., saline p.o.+WAY 100635 1 mg/kg i.p., carvedilol 10 mg/kg p.o.+saline i.p., respectively once per day for one week, while rats in vehicle group received saline p.o. and saline i.p. at the same timepoint.

4) After one-week treatment, portal pressure of all the rats were measured and rats were sacrificed for liver tissues.

3. Measurement of Portal Pressure in Rats

Similar as that in embodiment example 1.

4. Histologically Examination of Rat Livers

Similar as that in embodiment example 1.

5. Statistically Analysis

Similar as that in embodiment example 1.

6. Results

Figure 5:
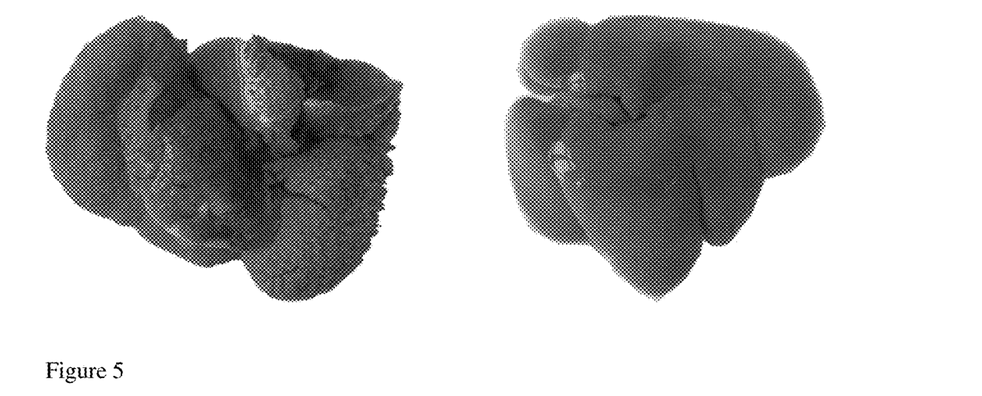
FIG. 5 shows representative images of livers from carbon tetrachloride (CCl4) induced cirrhotic rats (left) and normal controls (right).

1) Gross Morphology of Livers from CCl$_4$ Induced Cirrhotic Rats and Normal Controls Liver specimens were obtained after CCl$_4$ induction, treatment, and measurement of portal pressure. As shown in FIG. 5 from general observation, livers from CCl$_4$ group had a significant small size and nodular hyperplasia on the surface of liver, while livers from normal controls had smooth surface without nodular hyperplasia.

Figure 6:
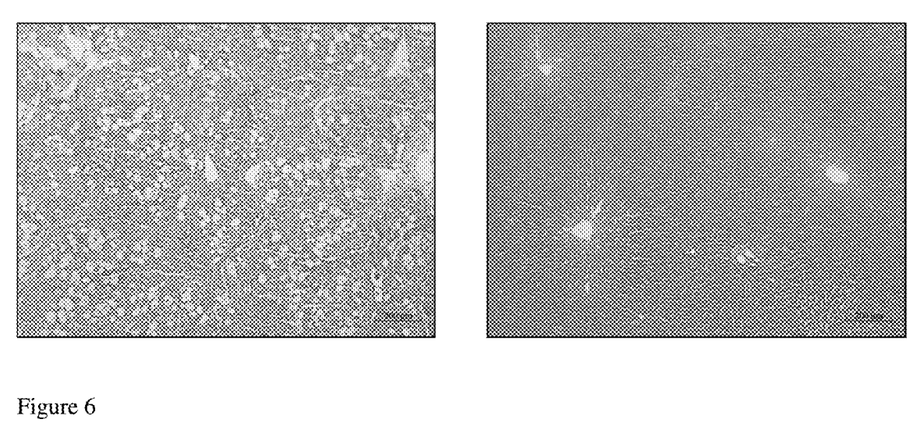
FIG. 6 shows representative images of HE staining of liver sections in $CCl_4$ induced cirrhotic rats (left) and normal controls (right).

2) HE Staining of Livers from CCl$_4$ Induced Cirrhotic Rats and Normal Controls As shown in FIG. 6, HE staining showed normal histology of liver with normal lobules, portal area, and interlobular septum in the liver from normal rats. In the CCl$_4$ induced cirrhotic rats, parenchymal fibrous tissue and pseudo-lobules were found in livers.

Figure 7:
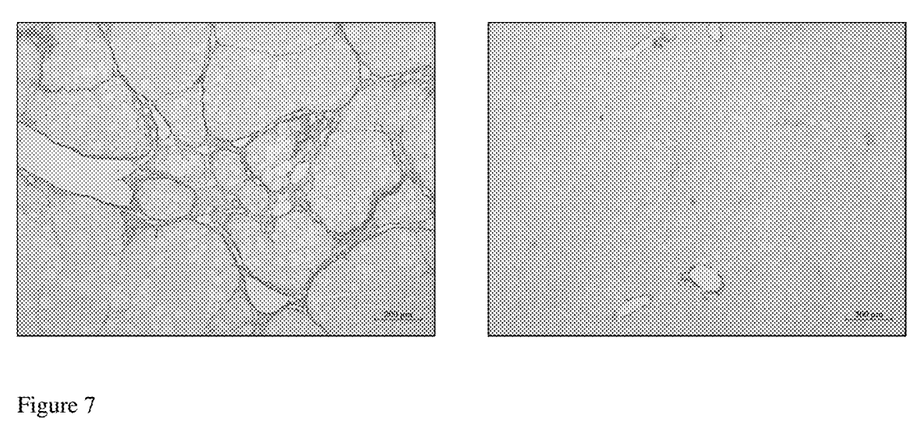
FIG. 7 shows representative images of Sirius Red staining of liver sections in $CCl_4$ induced cirrhotic rats (left) and normal controls (right).

3) Sirius Red Staining of Livers from CCl$_4$ Induced Cirrhotic Rats and Normal Controls As shown in FIG. 7, Sirius red staining showed there were a large amount of collagen deposition in the livers from CCl$_4$ induced cirrhotic rats, while only a little collagen deposition was found in the normal interlobular septum and portal area in the livers from normal controls.

Figure 8:
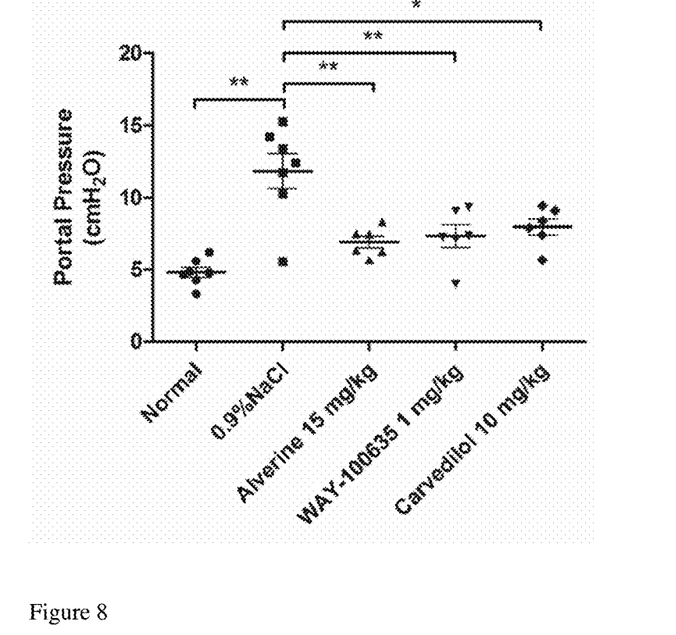
FIG. 8 shows effects of alverine and WAY 100635 on PP in cirrhotic portal hypertensive rats induced by $CCl_4$. PP: Vehicle vs. Normal control, P<0.01; Alverine vs. Vehicle, P=0.0065; WAY 100635 vs. Vehicle, P=0.0125; Carvedilol vs. Vehicle, P=0.0200.

4) Portal pressure of rats in different groups were showed in FIG. 8 and Table 2. Portal pressure: Vehicle vs. Normal control, P<0.01; Alverine vs. Vehicle, P=0.0065; WAY 100635 vs. Vehicle, P=0.0125; Carvedilol vs. Vehicle, P=0.0200.

TABLE 2

Portal pressure of rats in CCl$_4$ model.

| Groups | Portal pressure (cmH$_2$O) |
|---|---|
| Normal controls | 4.81 ± 0.93 |
| Vehicle | 11.85 ± 3.22 |
| Alverine | 6.94 ± 0.98 |
|  | (−41.44%*, P = 0.0065) |
| WAY10063 | 7.36 ± 2.14 |
|  | (−37.88%[#], P = 0.0125) |
| Carvedilol | 7.99 ± 1.37 |
|  | (−32.58%[#], P = 0.0200) |

*vs. Vehicle, Welch's t test;
[#]vs. Vehicle, Student't test.

As shown in Table 2, the selective antagonist of HTR1A WAY 100635 and alverine significantly decreased portal pressure of CCl$_4$ induced portal hypertensive rats comparing to that of normal controls. Additionally, the effect of WAY 100635 and alverine were not significantly different from that of carvedilol.

Example 3

Effects of the selective agonist of HTR1A 8-OH-DPAT on portal pressure (PP) in cirrhotic portal hypertensive rats induced by carbon tetrachloride (CCl$_4$).

1. Experimental Animals

Similar as that in embodiment example 1 and embodiment example 2.

2. Animal Model and Treatment

1) Twenty-three male Wistar rats, weighting 140 g to 160 g, were randomly divided into normal control group (N=8) and CCl$_4$ group (N=15). Rats in CCl$_4$ group were subjected to intraperitoneally (i.p.) injections of CCl$_4$ at 0.25 ml/kg (diluted 1:3 v/v in olive oil) twice per week for 12 weeks to induce cirrhotic portal hypertension, while the normal controls received injections of olive oil at the same timepoint. At the beginning of the eleventh week, rats in CCl$_4$ group were randomly divided into four groups: Vehicle group (N=8), and 8-OH-DPAT group (N=7).

2) 8-OH-DPAT (purchase from Selleck) was diluted in sterile normal saline at a concentration of 1 mg/ml and peritoneally injected (i.p.) into the rats in 8-OH-DPAT group.

3) Rats in the 8-OH-DPAT group were received 8-OH-DPAT 1 mg/kg i.p. once per day for one week, while rats in vehicle group received saline i.p. at the same timepoint.

4) After one-week treatment, portal pressure of all the rats were measured and rats were sacrificed for liver tissues.

b3. Measurement of Portal Pressure in Rats

Similar as that in embodiment example 1 and embodiment example 2.

4. Statistically Analysis

Similar as that in embodiment example 1 and embodiment example 2.

5. Results

Figure 9:
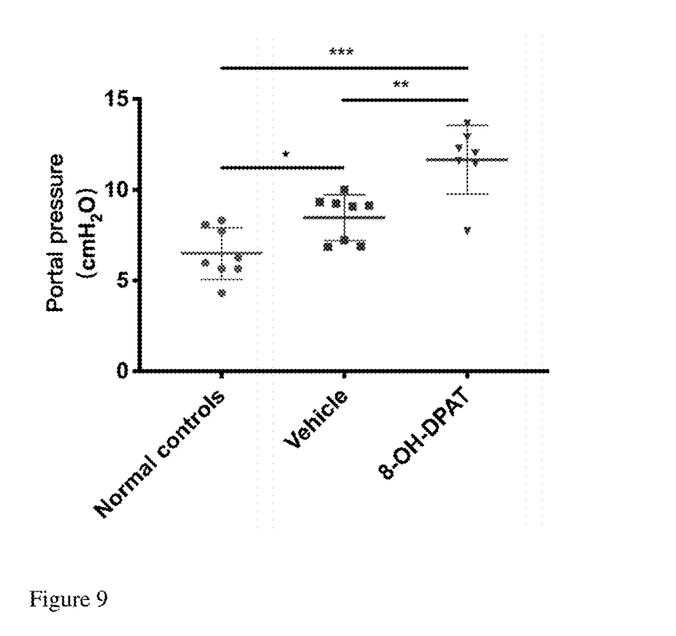
FIG. 9 presents effects of 8-OH-DPAT on PP in cirrhotic portal hypertensive rats induced by $CCl_4$. PP: Vehicle vs. Normal control, P=0.0107; 8-OH-DPAT vs. Normal control, P=0.0019; 8-OH-DPAT vs. Vehicle, P<0.0001.

Portal pressure of rats in different groups were showed in FIG. 9 and Table 3. Portal pressure: Vehicle vs. Normal control, P=0.0107; 8-OH-DPAT vs. Normal control, P=0.0019; 8-OH-DPAT vs. Vehicle, P<0.0001.

TABLE 3

Portal pressure of rats in CCl$_4$ model.

| Groups | Portal pressure (cmH$_2$O) |
|---|---|
| Normal controls | 6.50 ± 1.42 |
| Vehicle | 8.47 ± 1.27 |
| 8-OH-DPAT | 11.66 ± 1.89 |

As shown in Table 3, the selective agonist of HTR1A 8-OH-DPAT increased portal pressure of CCl$_4$ induced portal hypertensive rats comparing to that of normal controls.

Example 4

Effects of the selective agonist and antagonist of HTR1A on contractile tension of isolated portal vein.

1. Experimental Animals

Similar as that in embodiment example 1, embodiment example 2, and embodiment example 3.

2. Measurement of the Contractile Tension of Isolated Portal Veins

1) Male Wistar rats, weighting 140 g to 160 g, were anesthetized with inhalational isopentane through a mask. The portal veins were gently isolated from the animals and 3-5 mm of the vessel was removed under the anatomical microscope from the connective tissue, and then the vessel was placed in a cold Tyrode solution (NaCl: 148.9, KCl: 2.7, CaCl$_2$: 1.8, NaPO4H$_2$: 0.2, NaCO$_3$H: 11.9, MgCl$_2$: 1.2, glucose: 5.5 mM). Isolated portal veins were mounted in 20 ml jacketed tissue baths containing the appropriate Tyrode solution (37±0.5° C., PH=7.4) constantly bubbled with O2, by suspending them between two L-shaped stainless-steel hooks. The lower hooks were fixed and the upper hooks were attached to force-displacement transducers. Isometric force was measured and recorded using the ALC-MPA software associated with the equipment.

2) A pre-load of 1 g was applied. After mounting, isolated portal veins were equilibrated for 40 mM. The contractile response to depolarizing potassium solution was then assessed as a test for viability. The depolarizing KCl solution (80 mM) had the same composition as the Tyrode solution used, except for the NaCl that had been completely replaced by an equimolar amount of KCl. The iPVs were washed with Tyrode solution four times and re-equilibrated for another 20 mM.

3) To evaluate the effects of 5-HT or HTR1A agonist on the contraction of iPVs, serotonin or selective agonist of HTR1A (8-OH-DPAT and F11440) was directly administrated into the tissue baths for 3 minutes in cumulatively concentrations, and the magnitude of contractile tension was recorded. To evaluate the effects of HTR1A antagonist, a pre-incubation with selective antagonist of HTR1A (WAY 100635 and NAD 299) for 20 minutes was used before increasing administration of 5-HT or HTR1A agonist.

4) 5-HT, selective agonist of HTR1A (8-OH-DPAT and F11440), and selective antagonist of HTR1A (WAY 100635 and NAD 299) were purchased from Sigma, Selleck, Tocris, and TargetMol, respectively.

3. Results

Figure 10:
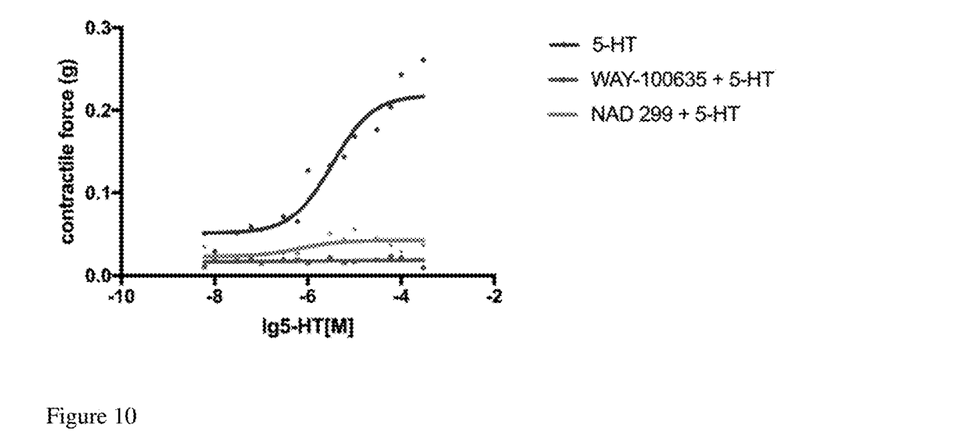
FIG. 10 presents dose-response curve for 5-HT and HTR1A selective antagonist (WAY 100635, NAD 299) on the constriction of isolated portal veins. The graph's horizontal axis shows the concentration of 5-HT expressed as the log 10 of the molar concentration, and the vertical axis shows the contractive tension of isolated portal vein.

1) As shown in FIG. 10, 5-HT induced a concentration-dependent contraction of isolated portal vein rings, which was abrogated by the pre-incubation of the selective antagonist of HTR1A (WAY 100635 or NAD 299) for 20 mM The graph's horizontal axis shows the concentration of 5-HT expressed as the log 10 of the molar concentration, and the vertical axis shows the contractive tension of isolated portal vein.

Figure 11:
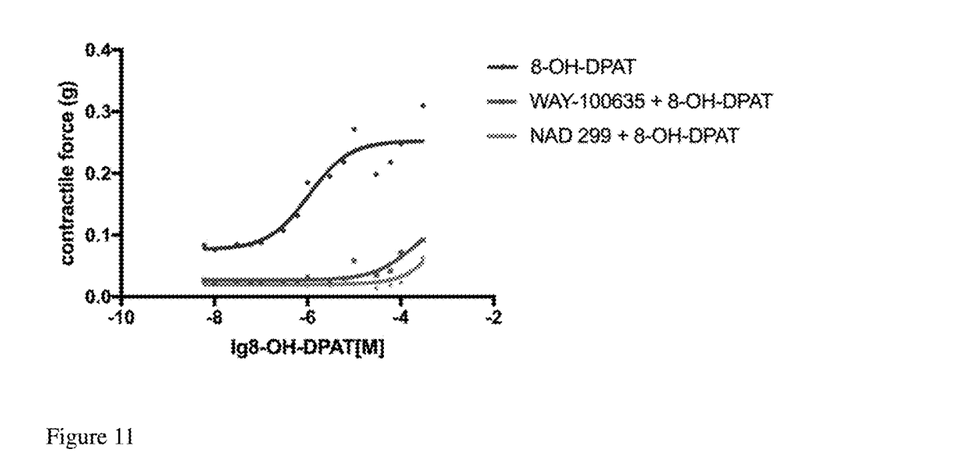
FIG. 11 presents dose-response curve for HTR1A selective agonist (8-OH-DPAT) and antagonist (WAY 100635, NAD 299) on the constriction of isolated portal veins. The graph's horizontal axis shows the concentration of 8-OH-DPAT, and the vertical axis shows the contractive tension of isolated portal vein.

2) As shown in FIG. 11, the selective agonist 8-OH-DPAT considerably increased the contractile force of iPVs in a concentration-dependent manner, which was almost completely inhibited by the selective antagonist of HTR1A (WAY 100635 or NAD 299). The graph's horizontal axis shows the concentration of 5-HT expressed as the log 10 of the molar concentration, and the vertical axis shows the contractive tension of isolated portal vein.

Figure 12:
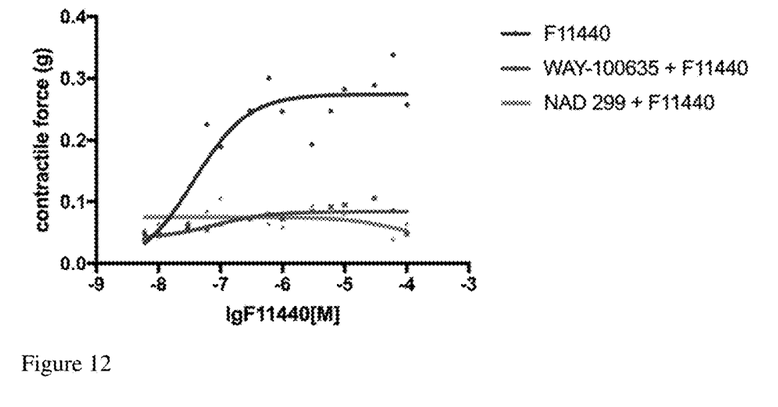
FIG. 12 presents concentration-response curve for HTR1A selective agonist F11440 and antagonist (WAY 100635, NAD 299) on the constriction of isolated portal veins. The graph's horizontal axis shows the concentration of F11440 expressed, and the vertical axis shows the contractive tension of isolated portal vein.

3) As shown in FIG. 12, the selective agonist F11440 considerably increased the contractile force of iPVs in a concentration-dependent manner, which was almost completely inhibited by the selective antagonist of HTR1A (WAY 100635 or NAD 299). The graph's horizontal axis shows the concentration of 5-HT expressed as the log 10 of the molar concentration, and the vertical axis shows the contractive tension of isolated portal vein.

Taken together, these data provide compelling evidence that HTR1A is critically involved in vasoconstriction of iPVs, further indicating that HTR1A plays a pivotal role in regulating portal pressure and targeting HTR1A will be a new treatment for portal hypertension.

While the invention has been particularly shown and described with reference to a preferred embodiment and various alternate embodiments, it will be understood by persons skilled in the relevant art that various changes in form and details can be made therein without departing from the spirit and scope of the invention.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method for treating portal hypertension and/or a complication thereof in a subject, comprising:
    administering to the subject in need thereof an effective amount of a pharmaceutical composition comprising alverine,
    wherein the complication of the portal hypertension is selected from the group consisting of esophageal-gastric varices, variceal hemorrhage, ascites, hepatic encephalopathy, experimental liver cirrhosis and a combination thereof.

2. The method of claim 1, wherein the pharmaceutical composition further comprises a pharmaceutically acceptable auxiliary.

3. The method of claim 1, wherein the pharmaceutical composition further comprises a pharmaceutically acceptable adjuvant that has no antagonistic effect with the alverine.

4. The method of claim 1, wherein an administration route is oral, intraperitoneal or intravenous.

5. The method of claim 1, wherein a dosage form of the pharmaceutical composition is selected from the group consisting of injection, capsule, tablet, powder, granules, pill, microcapsule or microsphere preparation, suppository, ointment, powder injection, aerosol, spray and targeted preparation.

* * * * *